US00PP10661P

United States Patent [19]

Heemskerk

[11] Patent Number: Plant 10,661

[45] Date of Patent: Oct. 27, 1998

[54] HOSTA PLANT NAMED 'ANNE'

[75] Inventor: Gerard J. C. M. Heemskerk, Noordwijk, Netherlands

[73] Assignee: Fa. W.J. Heemskerk & Zn., Noordwijk, Netherlands

[21] Appl. No.: 920,467

[22] Filed: Aug. 29, 1997

[51] Int. Cl.[6] ..... A01H 5/00

[52] U.S. Cl. ..... Plt./68.1

[58] Field of Search ..... Plt./54.1

[56] References Cited

U.S. PATENT DOCUMENTS

P.P. 2,467 1/1965 Grullemans ..... Plt./68.1
P.P. 7,046 10/1989 Ross ..... Plt./68.1
P.P. 8,015 10/1992 Falstad, III ..... Plt./68.1
P.P. 8,016 10/1992 Falstad, III ..... Plt./68.1

OTHER PUBLICATIONS

GTITM UPOVROM Citation for 'Anne' as per NL PBR HST0002, Aug. 16, 1996.

*Primary Examiner*—Howard J. Locker
*Assistant Examiner*—Kent L. Bell
*Attorney, Agent, or Firm*—C. A. Whealy

[57] ABSTRACT

A distinct cultivar of Hosta plant named 'Anne', characterized by its unique variegation pattern with relatively large light yellow margins; thick, rounded leaves; and numerous purple-striped flowers that are positioned well above the foliage on strong and erect peduncles.

5 Drawing Sheets

The present invention relates to a new and distinct cultivar of Hosta plant, botanically known as *Hosta fortunei,* and hereinafter referred to by the cultivar name 'Anne'.

The new cultivar was discovered by the inventor in Noordwijk, The Netherlands, as a naturally-occurring mutation of the nonpatented *Hosta fortunei* cultivar 'Aureo Marginata', and was observed as a single plant in a group of plants of the parent cultivar of July., 1988.

Asexual propagation of the new cultivar at Noordwijk, The Netherlands, by division and by tissue culture, has shown that the unique features of this new Hosta plant are stable and reproduced true to type in successive generations of asexual propagation.

The new Hosta has not been observed under all possible environmental conditions. The phenotype may vary somewhat with variations in environment such as temperature and light intensity, without, however, any variance in genotype.

The following traits have been repeatedly observed and are determined to be the unique characteristics of 'Anne'. These characteristics in combination distinguish 'Anne' as a new and distinct cultivar:

1. Unique variegation pattern with relatively large light yellow margins.
2. Thick, rounded leaves.
3. Numerous purple and light purple-striped flowers that are positioned well above the foliage on strong and erect peduncles.

The new Hosta can be compared to its parent cultivar, the cultivar 'Aureo Marginata'. The variegatiion pattern is different as plants of the new Hosta have a more uniform and larger light yellow margin. In addition, plants of the new Hosta grow faster and have thicker and more round leaves than plants of the cultivar 'Aureo Marginata'.

BRIEF DESCRIPTION OF THE PHOTOGRAPHS

The accompanying colored photographs illustrate the overall appearance of the new cultivar, showing the colors as true as it reasonably possible to obtain in colored reproductions of this type.

The first sheet of photographs comprises a top perspective view of a typical potted plant of 'Anne'.

The second sheet of photographs comprises a close-up view of typical leaves of 'Anne'.

The third sheet of photographs comprises a close-up view of typical leaves and flowers of 'Anne'.

The fourth sheet of photographs comprises a close-up view of typical flowers of 'Anne'.

The fifth sheet of photographs comprises a close-up view of a typical flower of 'Anne'. Leaf and flower colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe three-year old plants grown outdoors in Noordwijk, The Netherlands.

Botanical classification: *Hosta fortunei* cultivar 'Anne'.

Parentage: Naturally-occuring mutation of *Hosta fortunei* cultivar 'Aureo Marginata' (not patented).

Propagation:

*Method.*—By division and by tissue culture.

*Time to initiate roots from division.*—About 4 weeks.

*Time to initiate roots from tissue culture.*—About 4 weeks.

*Rooting habit.*—Freely branching, numerous fleshy roots.

Plant description:

*Plant shape.*—Mounding, dome-shaped, symmetrical.

*Growth habit.*—Upright and erect when young, becoming outwardly arching as leaves develop. Moderate to freely branching. Appropriate for 2-liter containers.

*Plant height.*—About 25 cm from soil level to top of leaf plane.

*Plant diameter.*—About 75 cm.

*Plant vigor and growth rate.*—Moderate to high.

*Crop time*.—Usually one year is required to produce a finished 2-liter plant under Northern European conditions.

*Foliage description*.—Leaf shape: Cordate with apiculate apex and cordate base. Leaf margin: Entire. Leaf texture: Leathery, smooth, glabrous. Older leaves weakly rugose. Leaf size: Length: About 16 cm. Width: About 12 cm. Venation pattern: Camptodrome. Leaf color: Center: Young and fully expanded, upper surface: 147A, becoming lighter, 147B, towards margin. Young and fully expanded, lower surface: 138A/138B, dull. Margin: Young, upper surface: 144B/144C. Young, lower surface: 144C. Fully expanded, upper surface: 151D. Fully expanded, lower surface: 8C. Older, upper surface: 10B. Older, lower surface: 11B. Petiole length, primary shoot: 21 to 23 cm. Petiole color: Center: 137C. Edge: Lighter than 151D.

Flower description:

*Flower arrangement*.—Clusters of single flowers with six fused petals arranged on a raceme. Flower peduncles arise from leaf axils. Typically three flower stems per plant. Flowering recurrent throughout the summer.

*Flower shape*.—Star-shaped.

*Flower diameter*.—About 3.5 cm.

*Flower depth* (*height*).—About 6 cm.

*Petals*.—Appearance: Satiny. Arrangement: Three interior, three exterior, fused. Apex: Apiculate. Margin: Entire. Texture: Smooth. Size: Length: About 4 cm. Width: About 1 cm. Color: upper and lower surfaces: White background with purple 87C/87D, stripes.

*Peduncle*.—Aspect: Strong and erect. Length: About 50 cm. Flowers held well above the foliage. Color: Dark green.

*Scape*.—Quantity: One. Shape: Lanceolate. Apex: Acute. Margin: Entire. Color: Green with reddish-brown at the margins.

*Reproductive organs*.—Androecium: Stamen number: Five. Anther size: About 4 mm. Anther color: Brownish black. Pollen color: Dark yellow. Gynoecium: Stigma color: White. Style color: White. Style length: About 6 cm.

Disease resistance: Not susceptible to root pathogens.

Seed development: Seed development is rarely observed.

It is claimed:

1. A new and distinct cultivar of Hosta plant named 'Anne', as illustrated and described.

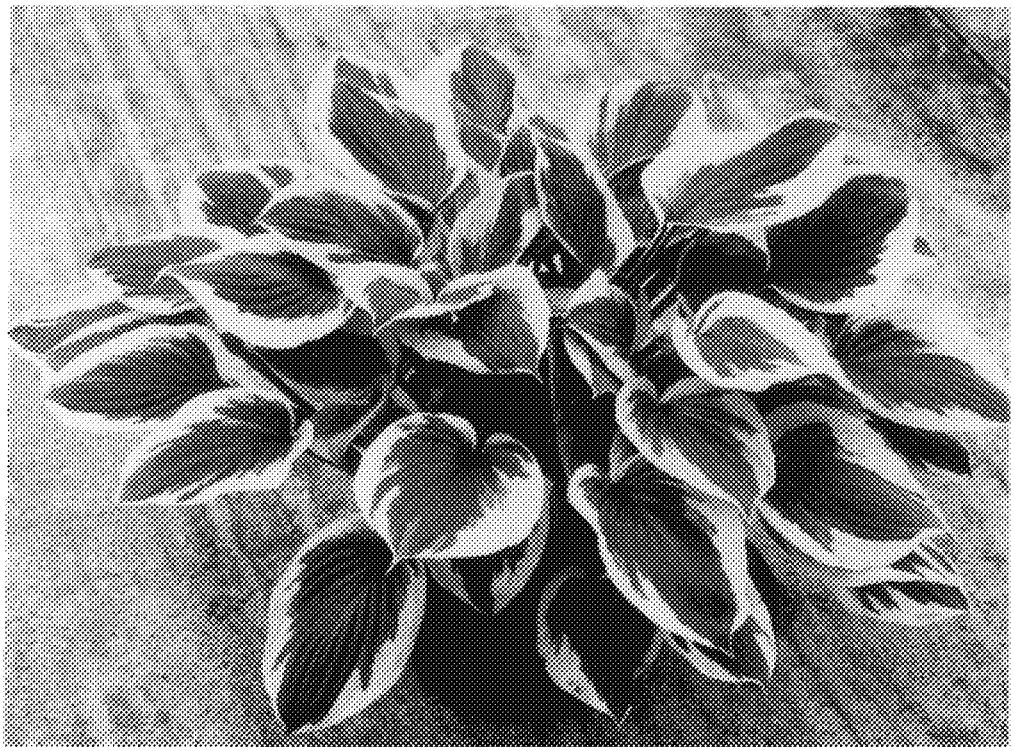

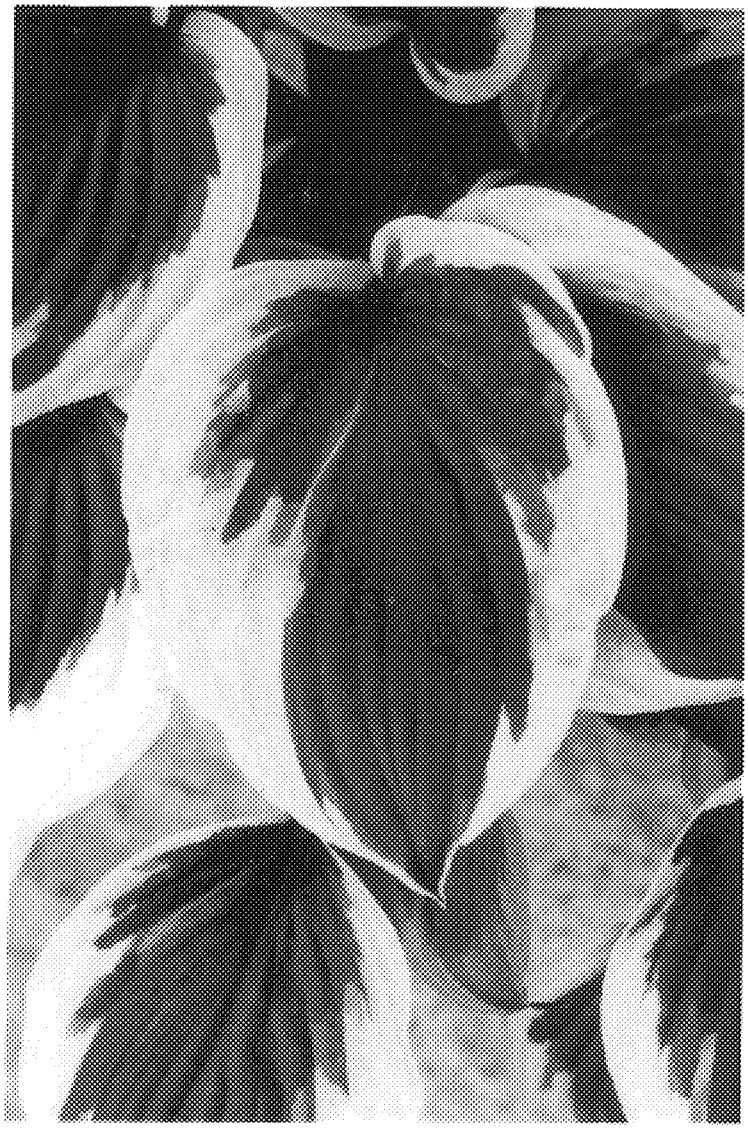

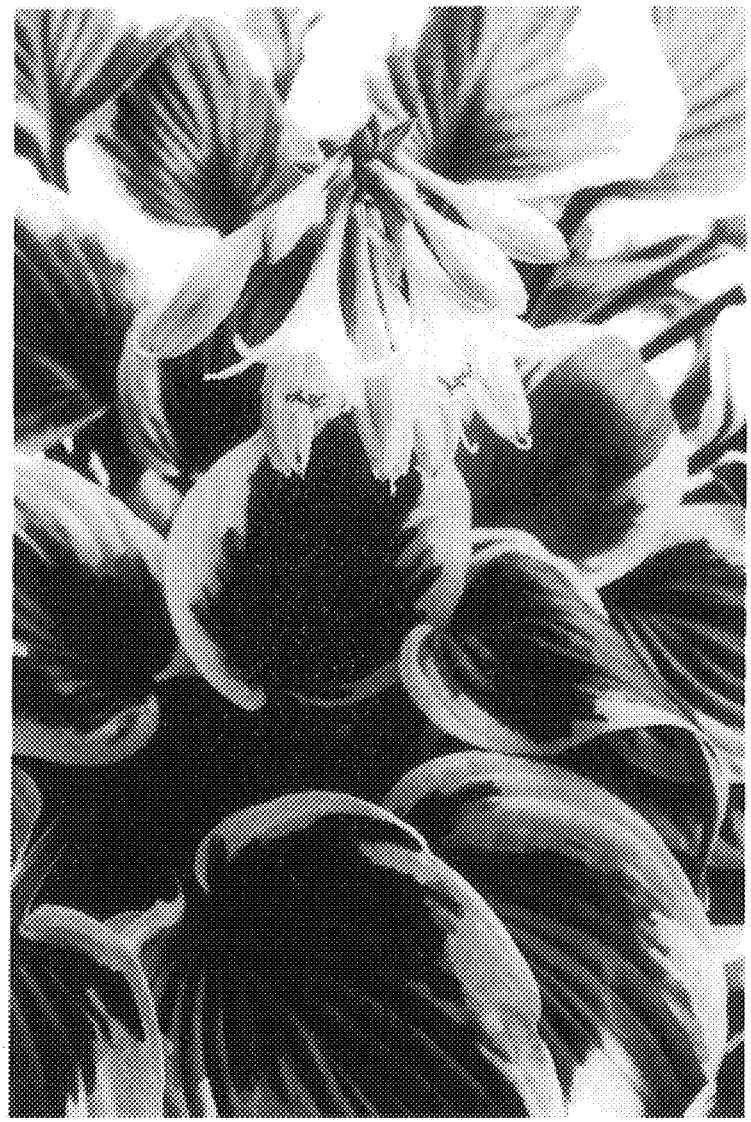

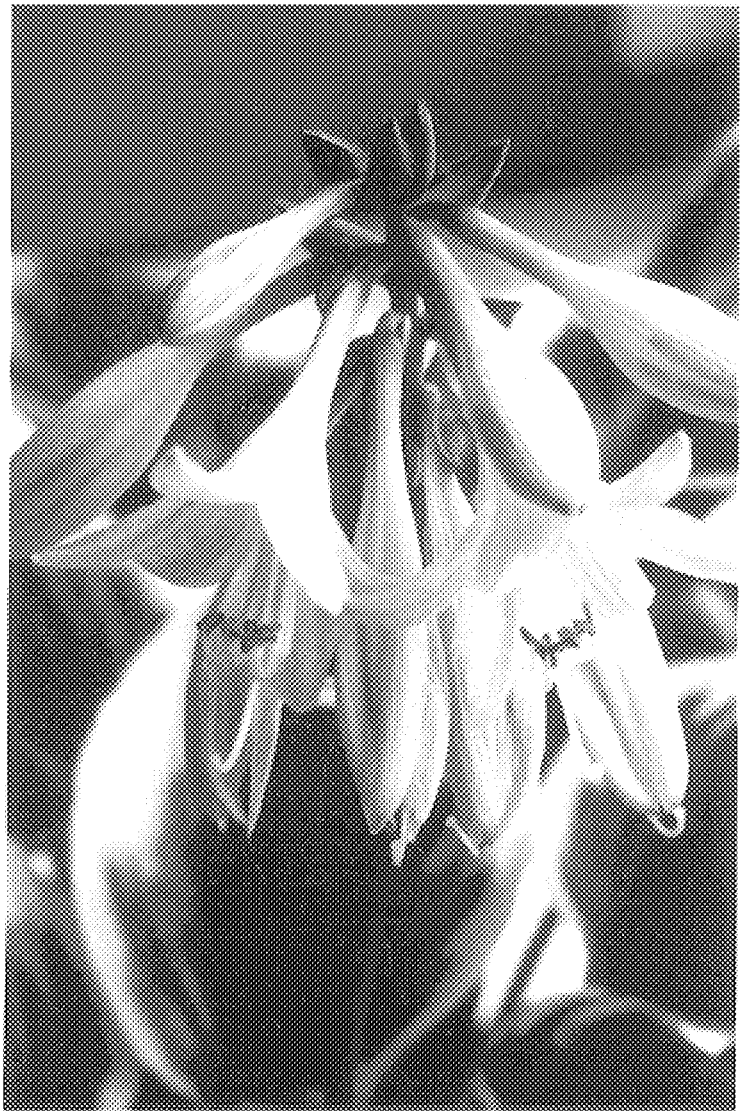

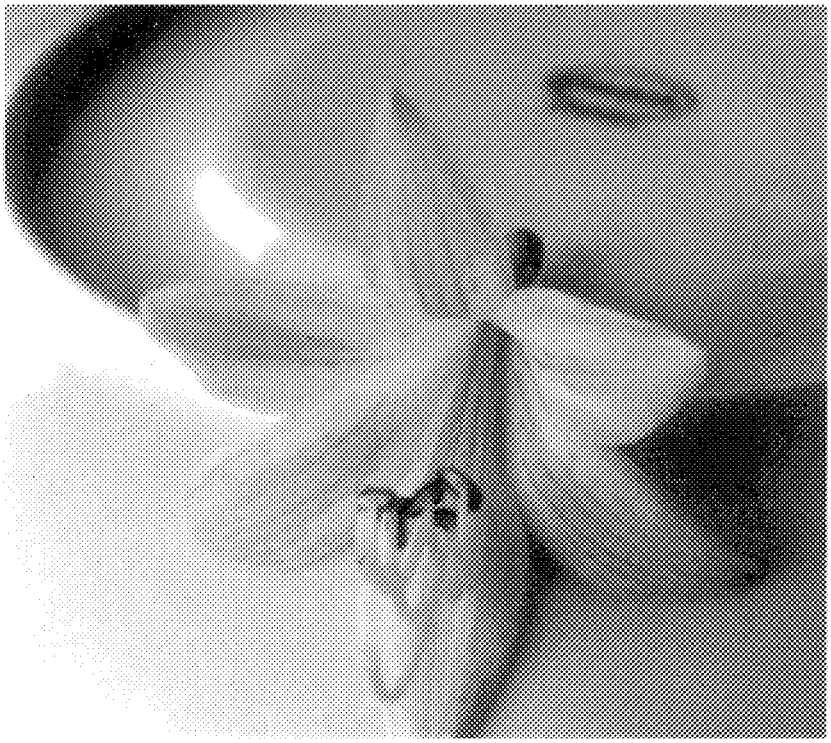

* * * * *